United States Patent [19]
Abrams et al.

[11] Patent Number: 5,547,982
[45] Date of Patent: Aug. 20, 1996

[54] ANTI-TUMOR PLATINUM COMPLEXES

[75] Inventors: Michael J. Abrams, Glenmoore; Gerald E. Bossard, King of Prussia; Robert C. Brooks, Pottstown; Geoffrey W. Henson; Jean F. Vollano, both of Exton, all of Pa.

[73] Assignee: Johnson Matthey, Inc., West Chester, Pa.

[21] Appl. No.: 396,164

[22] Filed: Feb. 27, 1995

[51] Int. Cl.$^6$ ............................. A61K 31/28; C07F 15/00
[52] U.S. Cl. .............................................. 514/492; 556/137
[58] Field of Search ............................. 556/137; 514/492

[56] References Cited

U.S. PATENT DOCUMENTS 4,882,447  11/1989  Tsujihara et al. ..................... 556/40

FOREIGN PATENT DOCUMENTS 0143883  6/1989  Japan.

*Primary Examiner*—Porfirio Nazario-Gonzalez
*Attorney, Agent, or Firm*—Cushman Darby & Cushman, LLP

[57] ABSTRACT

Platinum complexes, having anti-tumor activity, which include at least one functional ketone group or aldehyde, optionally conjugated as a linkable hydrazone complex. The functional ketone and aldehyde groups and the functionalized hydrazone complexes are linkable to antibodies, proteins, peptides and compounds having free amine, hydrazine or hydrazide functionality. Such agents are useful as targeted site-specific or disease specific chemotherapeutic agents.

13 Claims, No Drawings

ANTI-TUMOR PLATINUM COMPLEXES

The present invention relates to novel platinum complexes having anti-tumor activity.

More specifically, the invention relates to novel platinum complexes comprising at least one functional ketone group or aldehyde group, optionally conjugated as a linkable hydrazone complex. The functional ketone and aldehyde groups and the functionalized hydrazone complexes are linkable to antibodies, proteins, peptides and compounds having free amine, hydrazine or hydrazide functionality. Such agents are useful as targeted site-specific or disease specific chemotherapeutic agents.

The use of platinum complexes, especially cisplatin [cis-diamminedichloroplatinum (II)] and certain analogs thereof, in the chemotherapeutic treatment of cancer is now an established clinical technique, although efforts persist to find improved platinum complexes. The problem with such complexes, when administered as a composition together with an inert carrier or diluent, is that they are absorbed generally into the systemic circulation where they have a toxic effect on normal cells and tissues, as well as on the diseased cells and tissues which they are designed to treat. In practice, the maximum dose that can be administered is limited not by pharmaceutical effectiveness but by toxicity and adverse pharmacology.

These problems can be overcome by linking platinum complexes to targeting agents which render the complexes site-specific or disease-specific. It is the general object of the present invention to provide novel platinum complexes which, inter alia, can be linked to targeting agents to form site-specific or disease-specific platinum conjugates.

It is a further object of the present invention to provide a method of linking these complexes to the targeting agents.

A further object of this invention is to provide a method using these targeted complexes to inhibit or arrest the growth of tumors in animals.

Still other objects of the invention include the provision of a pharmaceutical composition suitable for use in the treatment of cancer, and a method for its administration.

Further objects and advantages of the present invention will be clear to one skilled in the art from a reading of the description that follows.

As noted above, the present invention provides platinum complexes comprising at least one functional ketone or aldehyde group, or functionalized hydrazone complex derived from the ketone or aldehyde complexes. These complexes are illustrated by Class I-IV described hereafter.

The Class I complexes have the functional ketone group or aldehyde group linked to the platinum through an amine group. These platinum complexes may be structurally shown as follows:

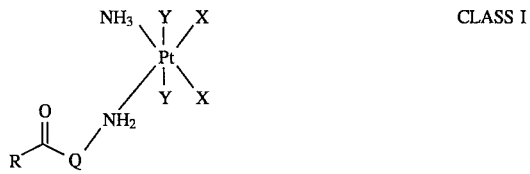

CLASS I where R is H, $CH_3$ or other lower alkyl of up to 6–8 carbons, alkenyl or alkynyl of like carbon content or aryl such as phenyl or naphthyl; Y is OH [Pt(IV)], Cl [Pt(IV)], $COOR^1$ [Pt(IV)] or absent [Pt(II)]; X is Cl, malonate, glycolate or oxalate; Q is a linking group such as $(CH_2)_n$ where n is 1–6, alkenyl or alkynyl of 3–6 carbons or substituted aryl, e.g. 1,4-diethylphenyl or like group, and $R^1$ is H, lower alkyl $(C_1-C_6)$ or aryl such as phenyl.

These compounds may be synthesized by the following illustrative routes:

Preparation of Pt(II)dichlorides

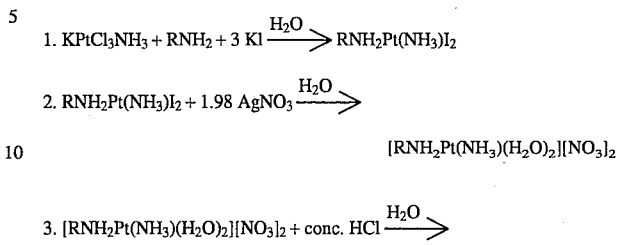

Preparation of Pt(IV)di and tetrachlorides

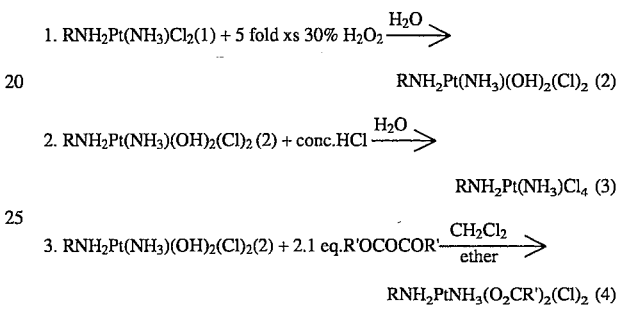

wherein R is aliphatic or aromatic aldehyde or aliphatic or aromatic ketone and R' is hydrogen, alkyl or aryl, e.g. $CH_3$ or like alkyl of up to 8 carbons, phenyl, or functionalized alkyl or aryl such as methoxyphenyl or carboxylate such as a succinate group, or the like.

Representative Class I compounds include (5-aminopentan-2 -one)ammino dichloro platinum (II), (5-aminopentan-2 -one)ammino dichloro dihydroxy platinum (IV), (5-aminopentan-2-one)ammino tetrachloro platinum (IV), (5-aminopentan-2-one)ammino diacetato dichloro platinum (IV), (2-aminoacetophenone)ammino dichloro platinum (II) and (2-aminoacetophenone)ammino platinum (II) and (2-aminoacetophenone)ammino tetrachloro platinum (IV), (5-aminopentan-2-one)ammino platinum (II) malonate and (5-aminopentan-2-one)ammino dihydroxy platinum (IV) malonate The following Examples I-VII are representative of the Class I embodiment of the invention:

EXAMPLE I

Preparation of 5-phthalimido-2-pentanone ethylene ketal

Sixty grams of 5-chloro-2-pentanone ethylene ketal (0.36 moles) was placed in 120 ml of DMF. Then 67.8 g (0.36 moles) of potassium phthalmide was added and the solution was brought to reflux with stirring for 14 hours. Upon cooling to room temperature, the reaction mixture had 300 ml of chloroform added and the resulting mixture was added to 300 ml of water. The aqueous layer was separated and washed with two 150 ml portions of chloroform. The chloroform fractions were combined and dried over anhydrous sodium sulfate. Evaporation of the chloroform solution afforded an oil which was dissolved in a minimal amount of acetone. Next, ether was added until a solid began to form and then the solid and solution were cooled to 0° C. for 18 hours. The solid was then filtered off, washed with ether and air dried.

71.4 g (0.25 moles) of 5-phthalimido-2-pentanone ethylene ketal

EXAMPLE II

Preparation of 5-amino-2-pentanone ethylene ketal

Seventy-one grams of 5-phthalimido-2-pentanone ethylene ketal (0.26 moles) were suspended into 250 ml of 95% ethanol. Then 13.0 g of $NH_2 \cdot NH_2 \cdot H_2O$ (0.26 moles) was added and the reaction mixture was brought to reflux. The stirred mixture was refluxed for 2 hours. Ether (400 ml) was added to the cooled suspension, which was then treated with 40 g of potassium hydroxide in 150 ml of water. The two layers were separated and the aqueous The ether was combined and dried over sodium sulfate. The solvent was then removed under pressure and the remaining liquid that contained crude product was weighed.

26.3 g of crude 5-amino-2-pentanone ethylene ketal

EXAMPLE III

Preparation of cis ammino-5-amino-2-pentanone ethylene ketal chloroiodo-platinum (II)

Potassium amminotrichloro platinate (II) (64.1 g; 0.18 moles) was dissolved in water and an aqueous solution of 0.18 moles of potassium iodide was added. Immediately after addition of the potassium iodide, the 26.3 g of crude 5-amino-2-pentanone ethylene ketal (0.18 moles) was added and a yellow solid resulted. The reaction mixture was stirred for half an hour after which the bright yellow solid was filtered off, washed first with 100 ml of ethanol then 300 ml of ether and air dried.

58.93 g (0.11 moles) of cis ammino 5-amino-2pentanone ethylene ketal chloroiodo platinum (II)

| | Analysis: | | | | |
|---|---|---|---|---|---|
| | C | H | N | Cl | I |
| % Calc. | 16.18 | 3.49 | 3.39 | 6.82 | 24.40 |
| Found | 16.21 | 3.52 | 3.35 | 6.88 | 24.30 |

EXAMPLE IV

Preparation of cis ammino-5-aminopentan-2-one dichloro platinum (II)

The cis ammino-5-amino-2-pentanone ethylene diketal chloroiodo platinum (II) (38.5 g; 0.11 moles) was suspended in 400 ml of water. The suspension was stirred and 5 ml of ethanol was added dropwise to wet the suspension. Next 38.2 g of silver nitrate (0.21 moles), dissolved in a minimal amount of water, was slowly added, after which the reaction mixture had its pH adjusted to 1 with nitric acid to deprotect the diketal. The reaction dissolved in a minimal amount of water, was slowly added, after which the reaction mixture had its pH adjusted to 1 with nitric acid to deprotect the diketal. The reaction proceeded in the dark for 12 hours after which the silver chloride and silver iodide formed was filtered off. The filtrate then had 30 ml of concentrated hydrochloric acid added to it and the reaction proceeded with stirring for 1 hour, after which a pale yellow precipitate was filtered off, washed with ether and air dried.

38.1 g (0.099 moles) of cis amino-5-amminopentan-2-one-dichloro-platinum (II)

| | Analysis: | | | |
|---|---|---|---|---|
| | C | H | N | Cl |
| % Calc. | 15.63 | 3.67 | 7.29 | 18.46 |
| Found | 15.72 | 3.71 | 7.22 | 18.49 |

$^1$H NMR (300 MHz; DMF-d$_7$; δ); 1.98 (2H, m), 2.10 (3H, s), 2.7–2.5 (4H, m).

EXAMPLE V

Preparation of cis, trans, cis ammino 5-aminopentan-2-one dihydroxy dichloro platinum (IV)

Thirty-eight grams (0.099 moles) of cis ammino-5-aminopentan-2 -one dichloro platinum (II) were suspended in 350 ml of water. Five milliliters of ethanol were added to wet the solid. Next 49 ml of a 30% solution of hydrogen peroxide (0.49 moles) was added with stirring.

The reaction stirred at room temperature for 5 hours. Then the solution was evaporated to 100 ml and absolute ethanol was added until a solid appeared. The reaction mixture was then placed at 0° C. for 10 hours. The pale yellow solid was filtered off, washed with ether and air dried.

26.2 g (0.063 moles) of cis, trans, cis amino-5-aminopentan2 -one dihydroxydichloro platinum (IV)

| | Analysis: | | | |
|---|---|---|---|---|
| | C | H | N | Cl |
| % Calc. | 14.35 | 3.82 | 6.70 | 16.96 |
| Found | 14.44 | 3.86 | 6.61 | 17.02 |

EXAMPLE VI

Preparation of cis, trans, cis ammino 5-aminopentan-2-one tetrachloro platinum (IV)

Twenty-six grams of cis, trans, cis ammino 5-aminopentan-2 -one-dihydroxy dichloro platinum (IV) (0.06 moles) were suspended in 80 ml of water. Next, an excess of concentrated hydrochloric acid (25 ml) was added, and immediately all the solid dissolved. The reaction was stirred at room temperature for 30 minutes and then the solvent was evaporated until a viscous yellow oil remained. The oil was dissolved in ethanol and ether was added until a solid appeared. Then the reaction mixture was cooled to 0° C. for 10 hours. The bright yellow solid was filtered off, washed with ether and air dried.

24.0 g (0,052 moles) of cis, trans, cis ammino-5-aminopentan-2 -one tetrachloro platinum (IV)

| | Analysis: | | | |
|---|---|---|---|---|
| | C | H | N | Cl |
| % Calc. | 13.20 | 3.10 | 6.16 | 31.16 |
| Found | 13.45 | 3.13 | 6.07 | 30.92 |

$^1$H NMR (d-DMF; δ); 2.05 (2H, m); 2.12 (3, s); 2.65 (2H, t); 2.90 (2H, m).

EXAMPLE VII

Preparation of Ammino(4-Aminobutanal) Tetrachloro Platinum (IV) (JM2679)

8.32 g (23.3 mmol) of Potassium[ammino trichloro platinum(II)] was stirred in 80 mL of acetone with 7.53 g (22.2 mmol)of TBA (HSO$_4$). A grey solid was removed by filtration and the orange filtrate taken to dryness on a rotovap. 4.00 g (25.4 mmol) of (EtO)$_2$CH(CH$_2$)$_3$NH$_2$ (90%) was added in 20 mL of methanol and 50 mL of diethyl ether. The mixture was allowed to stand for 5 days when a yellow solid was filtered off and washed with methanol and ether. 3.18 g (7.16)mmol–32.2%) of (NH$_3$)((EtO)$_2$CH(CH$_2$)$_3$NH$_2$)Pt(II)Cl$_2$ were recovered and used directly.

The solid was suspended in 20 mL of 1:1 Acetone:water and 7.82 mL of 30% H$_2$O$_2$ was added and the solution allowed to stir for 1 hour at room temperature. The solution was placed in the freezer overnight. The suspension was filtered and washed with acetone, ether and air dried to give 2.08g (4.51mmol) of (NH$_3$)((EtO)$_2$CH(CH$_2$)$_3$NH$_2$)Pt(IV)(Cl)$_2$(OH)$_2$.

The solid was dissolved into 75 mL of methanol to which 2.74 mL (38.34 mmol–8.5 x/s) of acetyl chloride and 11.6 mL (92.4 mmol) 2,2'-dimethoxypropane were added and allowed to react at room temperature for 2 days. Solvent and excess reagents were removed with the aid of a rotovap and the residue washed with ether and taken to dryness. The residue was deprotected by suspending it in 10 ml of acetonitrile to which was added 0.75 mL of 2:1 TFA:H$_2$O in 5 mL of acetonitrile. The mixture was stirred for 1 day and the yellow solid removed by filtration, washed with acetonitrile and ether and air dried. 0.94 g (2.13 mmol–47.3% from hydroxy compound) of a yellow solid were collected. Calculated C$_4$H$_{12}$N$_2$OCl$_4$Pt. Requires: C; 14.19%, H; 3.06% N; 8.28%, Cl; 29.82%. Found: C; 14.45%, H; 3.00%, N; 8.18%, Cl; 28.59%. $^1$H NMR (80 MHz; DMF-d$_7$; δ): 9.65 (1H, s), 6.8–4.8 (5 NH, m), 2.9–2.6 (2H, m), 2.4–2.2 (2H, t), 1.9–1.8 (2H, m).

The Class II complexes of the invention have the functional ketone or aldehyde group linked to platinum through functionalized malonic acid or equivalent leaving group dicarboxylate function. The Class II complexes may be structurally illustrated as follows:

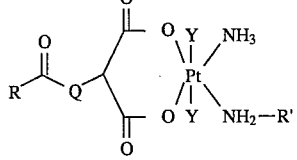

CLASS II wherein R, Y, Q and n have the values given earlier for the Class I compounds and R' is H, an aliphatic group, an aromatic group or a cyclic aliphatic group. These compounds may be synthesized as follows:

Preparation of Pt(II)dichlorides 1. (NH$_3$)Pt(NH$_2$R')I$_2$ + 1.98 AgNO$_3$ $\xrightarrow{H_2O}$

[(NH$_3$)Pt(NH$_2$R')(H$_2$O)$_2$][NO$_3$]$_2$

2. [(NH$_3$)Pt(NH$_2$R')(H$_2$O)$_2$][NO$_3$]$_2$ +

RC(O)(CH$_2$)$_n$CH(COO)$_2$K$_2$ + H$_2$O $\longrightarrow$

RC(O)(CH$_2$)$_n$CH(COO)$_2$Pt(NH$_3$)NH$_2$R' (6)

3. (6) + 5 fold xs 30% H$_2$O$_2$ $\longrightarrow$

RC(O)(CH$_2$)$_n$CH(COO)$_2$Pt(OH)$_2$(NH$_3$)NH$_2$R' (6A)

4. (6) + 2.1 eq. ROCOCOR $\xrightarrow[\text{ether}]{CH_2Cl_2}$

RC(O)(CH$_2$)$_n$CH(COO)$_2$Pt(COOR)$_2$(NH$_3$)NH$_2$R' (6C)

5. (6) + Cl$_2$ $\longrightarrow$

RC(O)(CH$_2$)$_n$CH(COO)$_2$Pt(Cl)$_2$(NH$_3$)NH$_2$R' (6B)

wherein R and R' have the values given above. Representative alkyl includes, for example, alkyl of up to 8 carbons. Other aliphatic, aromatic or cyclic groups include substituted alkyl, alkenyl, phenyl, cyclohexyl or the equivalent. Representative Class II complexes include the following:

diammino platinum (II) (δ-acetopropylmalonate)

diammino dihydroxy platinum (IV) (δ-acetopropylmalonate)

ammino cyclohexylamine platinum (II) (δ-acetopropylmalonate)

(3-aminopropanol)ammino platinum (II) (δ-acetopropylmalonate)

The preparation of the Class II complexes is illustrated by Example VIII.

EXAMPLE VIII

Preparation of cis ammino cyclohexylamino (δ-acetylpropyl malonate) platinum (II)

Two grams of cis amino cyclohexylamino platinum (II) diiodide were suspended in 50 ml of water and to this was added 1.98 equivalents of AgNO$_3$. The reaction stirred in the dark for 12 hours and the precipitated AgI was filtered off. The filtrate was placed in a round bottom flask and 2.1 equivalents of the di potassium salt of δ-acetylpropyl malonate was added with stirring. After 4 hours, the solution was evaporated to dryness and ethanol was added to remove the potassium nitrate. The salt was filtered off and the filtrate had ether added. It was placed at 0° C. for 8 hours. The resulting white solid was filtered off and air dried.

0.6 g (0.002 moles) of cis ammino cyclohexylamino (δ-acetylpropyl malonate) platinum (II)

| | Analysis: | | |
|---|---|---|---|
| | C | H | N |
| % Calc. | 33.80 | 5.27 | 5.63 |
| Found | 33.64 | 5.34 | 5.52 |

The Class III complexes of the invention are characterized by having the ketone group as part of a cyclic ring linked to the platinum through an amine group. These complexes may be structurally illustrated as follows:

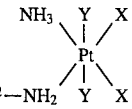

CLASS III wherein $R^2$ represents a cyclic aliphatic ketone ($C_4$–$C_{12}$), ketal, hemiacetal or acetal and X and Y have the values given earlier for the Class I compounds.

The Class III compounds may be made in the same way as the Class I compounds. Representative Class III compounds include (4-aminocyclohexanone)ammino dichloro platinum (II), (4-aminocyclohexanone)ammino dichloro dihydroxy platinum (IV), (4-aminocyclohexanone)ammino tetrachloro platinum (IV) and (4-aminocyclohexanone)ammino diacetato dichloro platinum (IV).

Preparation of the Class III complexes is illustrated by Examples IX to XIV:

EXAMPLE IX

Preparation of 1,4-amino cyclohexanone ethylene ketal

Ten grams of 1,4-cyclohexanodione mono-ethylene ketal (6.4 mmoles) were placed in 100 ml of dry methanol. Then 1 equivalent of $NH_4OH$ was added. The reaction proceeded for 2 days. The solution was then evaporated and the resulting oxime (oil) was dissolved in dry tetrahydrofuran (25 ml). The 4.14 grams of lithium aluminum hydride was added to 125 ml of dry tetrahydrofuran. The crude oxime (oil) dissolved in 25 ml tetrahydrofuran was added dropwise with stirring and the reaction proceeded at reflux for 30 minutes. After the reaction cooled, the excess lithium aluminum hydride was decomposed with water and then a 10% sodium hydroxide solution (20 ml) was added. The resulting sludge was placed in a soxhlet and extracted for 20 hours with 800 ml of ether. The ether was evaporated leaving an oil of crude product.

8.0 g of crude 1,4-amino cyclohexano ethylene ketal

EXAMPLE X

Preparation of cis ammino 1,4-amino-cyclohexanone ethylene ketal chloroiodo platinum (II)

Potassium ammino trichloroplatinate (II) (18 g; 50.4 mmoles) was dissolved in 250 ml of water. Two equivalents, 16 g, of potassium iodide was then added and immediately afterward the 8 grams of crude 1,4-aminocyclohexanone ethylene ketal was added to the mixture with stirring. After 20 minutes, a bright yellow solid was filtered off, washed with ethanol and ether and air dried.

13.4 g (25.2 mmoles) of cis ammino 1,4-aminocyclohexanone ethylene ketal chloroiodo platinum (II)

EXAMPLE XI

Preparation of cis ammino 1,4-amino-cyclohexanone dichloro platinum (II) monohydrate Four grams of cis ammino 1,4-amino-cyclohexanone ethylene ketal chloroiodo platinum (II) (7.5 mmoles) was suspended in 80 ml of water. Five ml of ethanol was added dropwise, with stirring, to wet the solid. Then 2.49 g of silver nitrate dissolved in a minimum amount of water was added and the reaction proceeded in the dark for 4 hours. After the first hour, the pH of the reaction mixture was adjusted to 1 with nitric acid. After the silver halides were filtered off, 15 ml of concentrated hydrochloric acid was added and the reaction stirred for 30 minutes. The resulting pale yellow solid was filtered and air dried.

2.5 g (6.0 mmoles) of cis ammino 1,4-aminocyclohexanone dichloro platinum (II) monohydate

|  | Analysis: | | | |
| --- | --- | --- | --- | --- |
|  | C | H | N | Cl |
| % Calc. | 17.40 | 3.89 | 6.76 | 17.12 |
| Found | 17.32 | 3.84 | 6.74 | 17.17 |

EXAMPLE XII

Preparation of cis, trans, cis ammino 1,4 aminocyclohexanone dihydroxy dichloro platinum (IV)

Four grams of ammino 1,4 amino-cyclohexanone dichloro platinum (II) monohydrate (9.6 mmoles) were suspended in 90 ml of water. Five ml of ethanol were then added dropwise, followed by dropwise addition of 5 equivalents of 30% hydrogen peroxide. The reaction mixture stirred for 5 hours and all the solid had completely dissolved. The solution was evaporated to 10 ml. Then 20 ml of water was added, followed by enough ethanol to afford precipitation of the product. The pale yellow solid was filtered off and air dried. The product was then put in a vacuum oven for 2 days to remove residual water.

2.7 g (5.8 mmoles) of cis,trans,cis ammino 1,4 aminocyclohexanone dihydroxy dichloro platinum (IV)

|  | Analysis: | | | |
| --- | --- | --- | --- | --- |
|  | C | H | N | Cl |
| % Calc. | 15.46 | 4.32 | 6.01 | 15.21 |
| Found | 15.69 | 4.21 | 5.97 | 15.06 |

EXAMPLE XIII

Preparation of cis,trans,cis ammino 1,4 aminocycohexanone tetrachloro platinum (VI)

One gram of cis,trans,cis ammino 1,4-aminocyclohexanone dihydroxy dichloro platinum (IV) (2.1 mmoles), was suspended in 20 ml of water with stirring. Then a twofold excess of concentrated hydrochloric acid was added. The solid dissolved immediately and the reaction was allowed to proceed for 10 minutes, after which the solution was evaporated to dryness. Next, absolute ethanol (10 ml) was added, followed by the addition of ether until a solid began to form. The mixture was cooled to 0° C. for 2 days and a bright yellow solid was filtered off. The solid was then dried under vacuum for 2 days to remove residual water.

0.6 g (1.3 mmole) of cis,trans,cis ammino 1,4-amino cyclohexanone tetrachloro platinum (IV)

|  | Analysis: | | | |
| --- | --- | --- | --- | --- |
|  | C | H | N | Cl |
| % Calc. | 15.43 | 3.03 | 6.00 | 30.36 |
| Found | 15.44 | 3.33 | 6.01 | 30.13 |

EXAMPLE XIV

Preparation of cis,trans,cis ammino 1,4-aminocyclohexanone diacetato dichloro platinum (IV)

Five hundred milligrams of cis,trans,cis ammino 1,4-aminocyclohexane dihydroxydichloro platinum (IV) (1.2 mmoles) was placed in 5 ml of acetic anhydride. Then 15 ml of ether were added and the reaction stirred for 2 days. The solid was filtered off, washed with ether and air dried.

0.32 g (0.62 mmoles) of ammino 1,4-aminocyclohexanone diacetato dichloro platinum (IV)

| | Analysis: | | | |
|---|---|---|---|---|
| | C | H | N | Cl |
| % Calc. | 23.36 | 3.92 | 5.43 | 13.7 |
| Found | 15.44 | 3.33 | 6.01 | 13.7 |

The Class IV embodiment of the invention comprises a Class I-III platinum complex conjugated with a hydrazine, hydrazide or amine to form linkable hydrazone platinum complexes. The Class IV products may be structurally illustrated as follows:

R—X—Z where Z is a platinum complex with pendant hydrazone linkage linked to R, a targeting molecule with or without X which is a linker group.

These complexes may also be illustrated by the formula:

Y—Z where Z is a platinum complex with pendant hydrazone linkage attached to Y, a linker containing a protein reactive group, e.g. NHS ester.

Representative of the Class IV compounds are the following:
ammino[4-succinimidyl-(4-aminobutanal)terephthalic hydrazone] dichloro platinum (II)
ammino[4-succinimydyl-(4-aminobutanal)terephthalic hydrazone] cyclobutanedioate platinum (II)
ammino [4-succinimydyl-(5-aminopentan-2-one) terephthalic hydrazone] tetrachloro platinum (IV)

The following examples illustrate the preparation of Class IV complexes representative of the invention:

EXAMPLE XV

Preparation of ammino [4-succinimidyl-(4-aminobutanol) terephthalic hydrazone] tetrachloro platinum (IV)

0.26 (0.59 mmol) of JM 2679 (see Example VII) was suspended in 7 mL of acetonitrile and 0.19 g (0.60 mmol) of succinimidyl-(4-hydrazinoterephthalate)hydrochloride (SHTH) was added. This was followed by the addition of 0.05 mL (0.62 mmol) of pyridine and 1 mL of DMF. After 5 hours, the solution was filtered to remove a small amount of white solid. 500 mL of ether was added to precipitate 0.12 g (0.17 mmol–28.8% recovery) of a yellow solid. Calculated $C_{16}H_{21}N_5O_5Cl_4Pt$–0.15 $(C_4H_{10}O)$. Requires: C; 28.03%, H; 22.50%, N; 9.84%, Cl; 19.93%. Found: C; 28.10%, H; 3.45%, N; 9.87%, Cl; 19.92%. $^1H$ NMR (80 MHz; DMF-$d_7$; δ): 8.23 (4H, s), 7.0–5.0 (5 NH, m), 3.03 (4H, s), 2.5–2.4 (2H, t), 2.2–2.1 (2H, t).

EXAMPLE XVI

Preparation of ammino [4-succinimidyl-(4-aminocyclohexanone) terephthalic hydrazone] tetrachloro platinum (IV)

0.19 g (0.54 mmol) of SHTH and 0.25 g (0.54 mmol) of ammino(4-aminocyclohexanone) tetrachloro platinum (IV) were stirred in 75 mL of 2:1 methanol:ethanol for 2 hours at room temperature in the dark. 500 mL of ether was added and 0.25 g (0.32 mmol–64.1%) of a yellow solid collected. Calculated $C_{18}H_{23}N_5O_5Cl_4Pt$–2$H_2O$–0.2 $(C_4H_{10}O)$. Requires: C; 29.04%, H; 3.73%, N; 9.01%, Cl; 18.26%. Found: C; 28.84%, H; 3.69%, N; 8.87, Cl; 18.19%.

The platinum complex of the invention may be coupled to targeting agents, which have free amine groups, hydrazine or hydrazide functionality. Example XVII below shows modification of a protein (monoclonal antibody) to introduce hydrazide functionality, followed by its coupling to the platinum complex by hydrazone formation.

EXAMPLE XVII

Platinum-Antibody Complex Formation

Two Step Procedure
Succinimidyl-(4-hydrazinoterephthalate)hydrochloride Modification Antibodies To a volume of antibody 2–10 mg/mL in 50 mM CHES pH 9.0 is added 2% of the antibody volume of succinimidyl-(4-hydrazinoterephthalate)hydrochloride (SHTH) in dry DMF. The concentration of SHTH, between 2.6–52 mM, in DMF is adjusted so that the molar excess of SHTH over antibody is twice the number of hydrazides per antibody desired. The reaction solution is stirred in the dark at 4° C. for a period of 4 to 5 hours. The excess SHTH and reaction side products are removed by either dialysis or column chromatography. Molar substitution ratios (MSR) of 0.1–16 can be achieved for monoclonal antibodies. Specific MSR's are dependent on the level necessary for any given targeting agent.
Ammino(5-Aminopentan-2-one) tetrachloro Platinum (IV) Modification of Antibody-SHTH Complex To a volume of antibody-SHTH complex at 5 mg/mL in 50 mM CHES pH 9.0 is added a 50 fold molar excess of ammino(5-aminopentan-2-one) tetrachloro platinum (IV), in dry DMF, over the number of hydrazides on the antibody. The concentration of ammino(5-aminopentan-2-one) tetrachloro platinum (IV) in DMF is such that the final concentration of DMF does not exceed 10% of the total volume. The reaction is stirred in the dark at 4° C. overnight. The excess ammino(5-aminopentan-2-one) tetrachloro platinum (IV) is removed by column chromatography on Trisacryl (GF05LS eluted with 50 mM sodium bicarbonate pH 8.5–9.0. These reaction conditions yield 70–75% modification of the hydrazides to form the hydrazone complexes, A preferred embodiment of the invention for coupling the platinum complexes to targeting agents involves the use of a preformed hydrazone complex with a protein reactive group. The modification of a targeting molecular (monoclonal antibody) is described below.

EXAMPLE XVIII

One Step Procedure
Ammino{4-succinimidyl-(5-aminopentan-2-one) terephthalic hydrazone} tetrachloro platinum (IV) Modification of Antibodies To a volume of antibody at 5–10 mg/mL in 50 mM CHES buffer pH 9.0, 5–10% of the antibody volume of ammino [4-succinimidyl -(5-aminopentan-2-one)terephthalic hydrazone] tetrachloro platinum (IV) in dry DMF was added. The concentration of the ammino[4-succinimidyl-(5-aminopentan-2 -one) terephthalic hydrazone] tetrachloro platinum (IV), 6.5 to 40 mM in DMF is adjusted so that the molar excess of ammino[4-succinimidyl-(5-aminopentan-2 -one) terephthalic hydrazone] tetrachloro platinum (IV) over antibody is approximately 2–4 times the number of platinum atoms per antibody required. The reaction is stirred in the dark for 4 hours at 4° C. The excess ammino[4-succinimidyl-(5-aminopentan-2-one) terephthalic hydrazone] tetrachloro platinum (IV) and reaction side products are removed by column chromatography on Trisacryl GF05LS, eluted with 50 mM sodium bicarbonate pH 8.5–9.0.

The complexes of the invention exhibit cytotoxicity against tumor cell lines. The cytotoxicity of representative compounds against the Daudi tumor cell line is shown in Table 1 below.

TABLE 1

CYTOTOXICITY OF LINKABLE PLATINUM COMPLEXES

| Structure | $CC_{50}(\mu M)^A$ |
|---|---|
| (structure) | 0.5 |
| (structure) | 0.55 |
| (structure) | 1.1 |
| (structure) | 0.1 |
| (structure) | 0.1 |
| (structure) | 0.3 |

TABLE 1-continued

CYTOTOXICITY OF LINKABLE PLATINUM COMPLEXES

| Structure | $CC_{50}(\mu M)^A$ |
|---|---|
| (structure) | 0.35 |
| (structure) | 0.008 |
| (structure) | 0.9 |
| (structure) | 0.2 |

$^A$Cytotoxicity testing against Daudi cells

The monoclonal antibody 5E9 modified with ammino[4-succinimidyl -(5-aminopentan-2-one) terephthalic hydrazone] tetrachloro platinum (IV) (AAtC) (MSR=8.9) showed selective targeting to Daudi cells. Targeting with the linkable antibody decreased the amount of platinum necessary to kill the tumor line by ~50 fold.

| Agent | $CC_{50}(\mu M)^*$ |
|---|---|
| 5E9-AAtCconjugate | 0.044 |
| AAtC | 2.1 |
| cis-Platinum | 0.91 |

*Concentration of platinum compound which killed 50% of the Daudi cells.

The complexes of the invention can be used in the treatment of tumors by administration in any conventional fashion in combination with a pharmaceutically acceptable carrier.

It will be appreciated that various modifications may be made in the invention as described above. Accordingly, the scope of the invention is defined in the following claims wherein:

What is claimed is:

1. A platinum complex selected from platinum complexes represented by one of the following structural formulas:

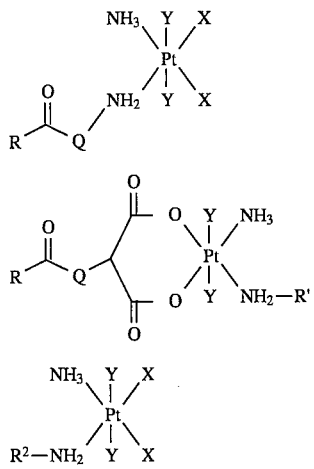

wherein R is H, lower alkyl of up to 8 carbons, alkenyl or alkynyl of up to 8 carbons or aryl; X is Cl, malonate, glycolate or oxalate; Y is OH, Cl, $COOR^1$ Lens B, or absent; Q is an alkylene, alkenyl, alkynyl or aryl linking group; R' is H, lower alkyl or aryl; R' is H, aliphatic, aromatic or cyclo aliphatic group and $R^2$ is a cyclic aliphatic ketone, ketal, hemiacetal or acetal.

2. The platinum complex of claim 1, selected from the group consisting of (5-aminopentan-2-one)ammino dichloro platinum (II), (5-aminopentan-2-one)ammino dichloro dihydroxy platinum (IV), (5-aminopentan-2one)ammino tetrachloro platinum (IV), (5-aminopentan-2one)ammino diacetato dichloro platinum (IV), (2-aminoacetophenone)ammino dichloro platinum (II) and (2-aminoacetophenone)ammino tetrachloro platinum (IV), (5-aminopentan-2-one)ammino platinum (II) malonate and (5-aminopentan-2-one)ammino dihydroxy platinum (IV) malonate.

3. The platinum complex of claim 1, selected from the group consisting of diammino platinum (II) (δ-acetopropylmalonate), diammino dihydroxy platinum (IV) (δ-acetopropylmalonate), ammino cyclohexylamine platinum (II) (δ-acetopropylmalonate) and (3-aminopropanol)ammino platinum (II) (δ-acetopropylmalonate).

4. The platinum complex of claim 1, selected from the group consisting of (4-aminocyclohexanone)ammino dichloro platinum (II), (4-aminocyclohexanone)ammino dichloro dihydroxy platinum (IV), (4-aminocyclohexanone)ammino tetrachloro platinum (IV) and (4-aminocyclohexanone)ammino diacetato dichloro platinum (IV).

5. The platinum complex of claim 1, selected from the group consisting of (4-aminobutanal)ammino dichloro platinum (II), (4-aminobutanal)ammino platinum (II) malonate and (4-aminobutanal)ammino tetrachloroplatinum (IV).

6. The platinum complex of claim 1, selected from the group consisting of ammino[4-succinimidyl-(4-aminobutanal)terephthalic hydrazone]dichloro platinum (II), ammino[4-succinimidyl-(4-aminobutanal)terephthalic hydrazone]cyclobutanedioate platinum (II) and ammino[4-succinimidyl-(5 -aminopentan-2-one)terephthalic hydrazone]tetrachloro platinum (IV).

7. A composition of matter comprising the platinum complex of claim 1 covalently linked to a targeting molecule via at least one functional ketone group or functional aldehyde group.

8. The composition of matter of claim 7, wherein at least one functional ketone group or functional aldehyde group is conjugated with a linkable hydrazone group.

9. The composition of matter of claim 7 wherein said targeting molecule is an antibody.

10. The composition of matter of claim 7 wherein said targeting molecule is a protein or peptide.

11. The composition of matter of claim 7 wherein said targeting molecule is a compound with cancer localizing properties.

12. A pharmaceutical composition suitable for use in inhibiting or arresting the growth of a tumor in a patient, said composition comprising as an active ingredient, a therapeutically effective amount of a platinum complex according to claim 1, together with a pharmaceutically acceptable carrier, diluent or vehicle.

13. A method of inhibiting or arresting the growth of a tumor in a patient, comprising administering to said patient a therapeutically effective amount of a platinum complex according to claim 1 under conditions such that said inhibition or arrest of growth is effective.

* * * * *